United States Patent [19]

Cooker et al.

[11] Patent Number: 5,770,746
[45] Date of Patent: Jun. 23, 1998

[54] EPOXIDATION PROCESS USING SUPPORTED SILVER CATALYSTS PRETREATED WITH ORGANIC CHLORIDE

[75] Inventors: Bernard Cooker, Malvern; Anne M. Gaffney, West Chester; Jennifer D. Jewson, Pottstown; Andrew P. Kahn, Eagleville; Rangasamy Pitchai, West Chester, all of Pa.

[73] Assignee: Arco Chemical Technology, L.P., Greenville, Del.

[21] Appl. No.: 880,896

[22] Filed: Jun. 23, 1997

[51] Int. Cl.⁶ .................................................. C07D 301/10
[52] U.S. Cl. ........................................ 549/534; 549/536
[58] Field of Search ................................ 549/534, 536

[56] References Cited

U.S. PATENT DOCUMENTS

| | | | |
|---|---|---|---|
| 2,194,602 | 3/1940 | Law et al. | 260/348 |
| 2,219,575 | 10/1940 | McNamee et al. | 260/348 |
| 2,279,469 | 4/1942 | Law et al. | 260/348 |
| 2,479,885 | 8/1949 | West | 252/415 |
| 3,888,889 | 6/1975 | Kolombos et al. | 260/348.5 |
| 4,007,135 | 2/1977 | Hayden et al. | 252/467 |
| 4,874,879 | 10/1989 | Lauritzen et al. | 549/536 |
| 5,155,242 | 10/1992 | Shankar et al. | 549/534 |
| 5,625,084 | 4/1997 | Pitchai et al. | 549/536 |
| 5,686,380 | 11/1997 | Pitchai et al. | 502/347 |

FOREIGN PATENT DOCUMENTS 1282772  4/1991  Canada.

*Primary Examiner*—C. Warren Ivy
*Assistant Examiner*—Garth M. Dahlen
*Attorney, Agent, or Firm*—Stephen D. Harper

[57] ABSTRACT

A propylene epoxidation process wherein a supported silver catalyst is utilized may be operated at high efficiency even in the absence of any organic chloride in the feedstream, provided the catalyst is first contacted at an elevated temperature with a treatment stream comprised of an organic chloride and molecular oxygen.

20 Claims, No Drawings

EPOXIDATION PROCESS USING SUPPORTED SILVER CATALYSTS PRETREATED WITH ORGANIC CHLORIDE

FIELD OF THE INVENTION

This invention relates to a process for the direct oxidation of propylene to propylene oxide in the vapor phase using molecular oxygen. In particular, the invention pertains to the use of a composition comprised of silver supported on an inert refractory solid to selectively catalyze the formation of epoxides. The performance of the catalysts is improved by exposure to a conditioning stream comprised of a $C_1$–$C_{10}$ organic chloride and molecular oxygen in the vapor phase. Pretreating the catalyst in this manner permits the epoxidation process to be operated with high selectivity in the absence of the organic chloride.

BACKGROUND OF THE INVENTION

The direct oxidation of ethylene to ethylene oxide by molecular oxygen is well-known and is, in fact, the method used currently for commercial production of ethylene oxide. The typical catalyst for such purpose contains metallic or ionic silver, optionally modified with various promoters and activators. Most such catalysts contain a porous, inert support or carrier such as alpha alumina upon which the silver and promoters are deposited. A review of the direct oxidation of ethylene in the presence of supported silver catalysts is provided by Sachtler et al. in *Catalyst Reviews: Science and Engineering*, 23 (1&2), 127–149(1981).

It is also well-known, however, that the catalysts and reaction conditions which are best suited for ethylene oxide production do not give comparable results in the direct oxidation of higher olefins such as propylene. The discovery of processes capable of providing propylene oxide by vapor phase direct oxidation in higher yields than are presently attainable thus would be most desirable.

Canadian Patent No. 1,282,772 describes a carbonate-supported catalytic system for alkene epoxidation. The feedstream for the process must contain, in addition to alkene and an oxygen-containing gas, a gas phase halogen compound such as an alkyl halide. The halogen compound is added to the feedstream in order to enhance the performance of the catalyst. According to the patent, the suitable concentration range for the halogen compound is about 5 to about 2000 ppm where the alkene is propylene. All of the propylene epoxidation examples in the patent utilized 200 ppm ethyl chloride.

Numerous other references have proposed the use of halogen compounds as feedstream additives to improve the efficiency of the direct silver catalyzed oxidation of alkenes to alkene oxides. See, for example, the discussion in the "Background Art" section of the aforementioned Canadian patent and in U.S. Pat. No. 2,279,469 (Law et al.). It is generally believed that optimum selectivity to propylene oxide in a silver-catalyzed direct oxidation process is only attainable if the feedstream contains a halogen compound. The scientific theory often advanced is that such compounds function as "repressants" or "anti-catalysts" by inhibiting to a controlled degree the oxidation activity of the catalyst so that over-oxidation of propylene to undesired by-products such as carbon dioxide is suppressed. However, it would be highly desirable to develop direct propylene epoxidation processes wherein the use of such halogen compounds during epoxidation is minimized or avoided altogether. Such substances, even at ppm levels, add significantly to the raw material costs associated with the production of propylene oxide. Moreover, the presence of halogen compounds in the feedstream tends to result in the generation of ionic chloride species in the recovery section of the process; such species promote corrosion of the metallic components of the recovery apparatus. Additionally, any halogen compound in the product stream exiting the epoxidation process must be rigorously removed in order to avoid the release of halogen contaminants into the general environment.

SUMMARY OF THE INVENTION

We have now unexpectedly discovered that it is possible to maintain relatively high yields of propylene oxide over an extended period of time in the complete absence of any organic chloride in the feedstream if the supported silver catalyst used to catalyze the direct oxidation of propylene is first exposed to a vapor phase stream containing both an organic chloride compound and molecular oxygen at an elevated temperature. This invention thus provides a method of operating a propylene epoxidation process comprising:

(a) contacting a supported silver catalyst with a treatment stream comprised of a $C_1$–$C_{10}$ organic chloride and molecular oxygen in the vapor phase at a temperature of from 150° C. to 350° C. for a time effective to incorporate chloride into the supported silver catalyst to form a chloride-containing catalyst, wherein the supported silver catalyst is comprised of (i) an inert refractory solid support, (ii) a catalytically effective amount of silver, and (iii) a promoting amount of a potassium promoter derived from a potassium salt comprising potassium cation and a nitrogen oxyanion or precursor thereof; and (b) contacting the chloride-containing catalyst with a feedstream comprised of propylene and molecular oxygen, but essentially free of $C_1$–$C_{10}$ organic chloride, for a time and at a temperature effective to form propylene oxide.

In an especially desirable embodiment of the invention, the support is comprised of an alkaline earth metal carbonate.

DETAILED DESCRIPTION OF THE INVENTION

The present invention is directed to a process for the vapor phase oxidation of propylene to propylene oxide, i.e., an epoxidation process performed in the presence of an oxygen-containing gas and a particular class of supported silver catalysts pretreated with a $C_1$–$C_{10}$ organic chloride such as ethyl chloride.

Any of the inert refractory solid materials known in the art as effective supports for silver-containing olefin oxidation catalysts may be utilized, including, for example, alumina (including alpha alumina), silicon carbide, silica, zirconia, titania, and the like. However, the support material most preferred for use in the present invention is an alkaline earth metal carbonate. Carbonates suitable for use include inorganic carbonates having a cation which is an alkaline earth metal ion, particularly calcium, strontium, magnesium or barium, with calcium carbonate being most preferred. Alkaline earth metal carbonate supports are described, for example, in Canadian Pat. No. 1,282,772.

Such support materials are capable of providing exceptionally high propylene oxide selectivities and have been found to be surprisingly superior to other support materials in this respect. The supports of the present invention may exist in various forms. In one embodiment, the support is one in which the alkaline earth metal compound is the predominant (i.e., at least 50% by weight) or, preferably, substantially the exclusive component of the support (i.e., the support consists essentially of one or more alkaline earth metal compounds). In other embodiments of the invention, the alkaline earth metal carbonate is used in conjunction with a solid substrate, i.e., a subsupport or substructure composed of a more conventional support material, such as alumina (preferably, alpha-alumina). However, the alkaline earth metal compound support material will normally comprise at least 25 weight percent (in most embodiments, at least 35 weight percent) of the finished catalyst.

The surface area of the support material generally is at least 0.6 m$^2$/g, preferably at least 1.5 m$^2$/g. However, alkaline earth metal compound support materials having relatively high surface areas (e.g., 50 to 100m$^2$/g) are also effective for the purposes of this invention. This result was surprising in view of the preference generally expressed in the direct olefin oxidation field for low surface area supports (typically, 0.03 to 10 m$^2$/g). The surface area is measured by the conventional B. E. T. method using nitrogen or krypton described by Brunauer, Emmett and Teller in *J. Am. Chem. Soc.* 60, 309–16 (1938).

The support materials used in the present invention may generally be described as porous or microporous and typically have water pore volumes of about 0.05 to 0.80 cc/g.

The supported catalyst used in the present invention may be prepared by any known method of introducing silver and/or a promoter in soluble form to a support. Suitable methods are described, for example, in Canadian Patent No. 1,282,772 and U.S. Pat. No. 5,625,084. A preferred method of introducing silver to the support is by an impregnation process in which a solution of a silver compound (which can be a salt or complex of silver) in an amount sufficient to deposit the desired weight of silver upon the support is dissolved in a suitable solvent or "complexing/solubilizing" agent. The solution may be used to impregnate the support by immersing the support in the silver compound-containing impregnating solution and forming a pasty mixture or slurry. The slurry is then dried and calcined by placing the mixture in an oven or furnace at about 100° to about 120° C. for 0.5 to 6 hours and then heating the mixture at a temperature of from about 250° to about 600° C. for another 1 to 6 hours. This procedure accomplishes drying of the support/silver mixture, removes volatile components and reduces the silver present to its elemental form.

The potassium salt and optional metal promoter compound(s) may be introduced to the catalyst, either simultaneously or separately, as impregnation solutions in a separate impregnation step or steps. Again, this may be done by any known manner of impregnating a porous material. Conveniently, this may be carried out by placing the catalyst material in a container, evacuating the container and thereafter introducing the solution(s). Alternatively, the support may be sprayed or sprinkled with the impregnating solution (s). The excess solution may then be allowed to drain off or the solvent may be removed by evaporation under reduced pressure at a suitable temperature. The catalyst may then be dried at a moderate temperature (e.g., at 120° C.) in a oven (one-half to five hours typically being sufficient). Such a procedure is known as a "sequential" or "consecutive" method of preparation. The alkaline earth metal compound-supported catalyst may also be prepared by a "simultaneous" or "coincidental" method of preparation. With this method, the potassium salt and the optional metal promoter compound(s) are included in the silver compound-containing solution used to impregnate the support. In yet another embodiment, the support is impregnated with the silver compound (optionally, also with one or more metal promoter compounds), calcined, impregnated with the potassium salt, and then dried without calcination.

The choice of silver compound used to form the silver-containing impregnating solution in a solvent or a complexing/solubilizing agent is not particularly critical and any silver compound generally known to the art which is both soluble in and does not react with the solvent or complexing/solubilizing agent to form an unwanted product may be employed. Thus, the silver may be introduced to the solvent or complexing/solubilizing agent as an oxide or a salt, such as nitrate, carbonate, or carboxylate, for example, an acetate, propionate, butyrate, oxalate, malonate, malate, maleate, lactate, citrate, phthalate, fatty acid ester, and the like or combinations thereof. In one embodiment, silver (I) oxide is utilized.

A large number of solvents or complexing/solubilizing agents may be suitably used to form the silver compound-containing impregnating solution. Besides adequately dissolving the silver compound or converting it to a soluble form, a suitable solvent or complexing/solubilizing agent should be capable of being readily removed in subsequent steps, either by a washing, volatilizing or oxidation procedure, or the like. The complexing/solubilizing agent, preferably, should also permit solution to provide silver in the finished catalyst to the extent of preferably about 2 to about 70 percent silver, based on the total weight of the catalyst. It is also generally preferred that the solvents or complexing/solubilizing agents be readily miscible with water since aqueous solutions may be conveniently employed. Among the materials found suitable as solvents or complexing/solubilizing agents for the preparation of the silver compound-containing solution are alcohols, including glycols, such as ethylene glycol, amines (including alkanolamines such as ethanolamine and alkyldiamines such as ethylene-diamine) and carboxylic acids, such as lactic acid and oxalic acid, as well as aqueous mixtures of such materials.

Typically, a silver compound-containing solution is prepared by dissolving a silver compound in a suitable solvent or complexing/solubilizing agent such as, for example, a mixture of water, ethylenediamine, oxalic acid, silver oxide, and monoethanolamine. The solution is then mixed with support particles and drained. Thereafter the particles are suitably dried.

As indicated above, after impregnation, the silver compound-impregnated support particles are treated to convert the silver compound to silver metal and thereby effect deposition of silver on the surface of the support. As used herein, the term "surface", as applied to the support, includes not only the external surfaces of the support but also the internal surfaces, that is, the surfaces defining the pores or internal portion of the support particles. This may be done by treating the impregnated particles with a reducing agent, such as hydrogen or hydrazine and/or by roasting, at an elevated temperature to decompose the silver compound and reduce the silver to its free metallic state. Certain solubilizing agents such as alkanolamines, alkyldiamines, and the like may also function as reducing agents.

Although at least a catalytically effective amount of silver must be present in the finished catalyst (meaning an amount that provides a measurable conversion of propylene to propylene oxide), the silver concentration preferably is from about 2 percent to 70 percent, by weight, based on the total weight of the catalyst. More preferably, the silver concentration ranges from about 10 to 60 percent by weight.

It has been unexpectedly discovered that the presence of potassium in the preparation of the supported silver catalyst significantly enhances the efficiency of said catalyst as a propylene epoxidation catalyst. Surprisingly, other alkali metals such as cesium which are well-known as promoters in the ethylene oxide art fail to improve catalyst performance to an appreciable extent. The potassium is introduced by means of a potassium salt, with the selection of particular anions as counter ions to the potassium cation being found to be critical to the attainment of optimum catalyst performance. The anion must be a nitrogen oxyanion (i.e., an anion or negative ion which contains both nitrogen and oxygen atoms such as nitrate or nitrite) or a precursor thereof. Potassium compounds containing species capable of being converted to nitrogen oxyanions under the catalyst preparation or epoxidation conditions (i.e., which are nitrogen oxyanion precursors) are thus also suitable for use. Carbon oxyanions such as carbonate and bicarbonate, for example, may be employed.

The efficiency-enhancing potassium salt may be introduced to the catalyst in any known manner. Thus, impregnation and deposition of silver and the potassium salt may be effected coincidentally or sequentially. For example, the support could be impregnated with a solution or solutions of the potassium salt and silver compound, dried, and then calcined to reduce the silver compound and generate the active supported silver catalyst. Alternatively, the support may be impregnated with the silver compound, dried, calcined, and then re-impregnated with the potassium salt.

In order to perform coincidental impregnation, the potassium salt must be soluble in the same solvent or complexing/solubilizing agent used with the silver impregnating solution. With a sequential procedure in which the silver is added first, any solvent capable of dissolving the salt which will neither react with the silver nor leach it from the support is suitable. Aqueous solutions are generally preferred, but organic liquids, such as alcohols, may also be employed. Suitable procedures for effecting introduction of a potassium salt to a solid support are well known in the art.

The potassium salt is used in an amount sufficient to provide a potassium promoter concentration which results in an improvement in one or more of the catalytic properties (e.g., selectivity, activity, conversion, stability, yield) of the supported silver catalyst as compared to a catalyst not containing the potassium promoter. The precise amount will vary depending upon such variables as the composition in the feed stream, the amount of silver contained in the catalyst, the surface area of the support, the process conditions, e.g., space velocity and temperature, and morphology of support. It has been found, however, that a minimum of at least 0.5 percent by weight of the potassium promoter, calculated as cation, based on the total weight of the catalyst must be present for the catalyst to exhibit a significant advantage over an analogous catalyst containing no potassium promoter. Potassium concentrations as high as 10 percent by weight may be utilized, although generally little additional benefit is realized beyond a concentration of 5 weight percent. More preferably, the potassium promoter level is an amount corresponding to about 1 to about 3 weight percent K.

An optional component of the supported silver catalysts used in this invention is a promoting amount of one or more metal promoters. Preferred metal promoters include Re, Mo, W and the like, either alone or in combination with other metal promoters. "Promoting amount" means an amount that works effectively to provide an improvement in one or more catalytic properties of a catalyst as compared to a catalyst not containing a metal promoter. The exact form of the metal promoters under epoxidation operating conditions is not known. The metal promoters, it is believed, are not present on the catalyst in the elemental form since the promoters are applied to the catalyst in the form of compounds (including ions, salts and/or complexes) and the reducing conditions generally used to reduce the silver to metallic silver are not usually sufficient to reduce the metal promoter compounds to the elemental form.

It is thought that the metal promoters deposited on the support or present on the catalyst are in the compound form, most probably in the form of oxygen-containing or oxidic compounds. In a presently preferred embodiment, the metal promoters are introduced to the catalyst in the oxyanionic form, i.e., in the form of anions, or negative ions which contain oxygen. Examples of anions of metals that can be suitably applied include the molybdates, tungstates and perrhenates. The anions can be prepared by the reactive dissolution of various non-anionic metal compounds such as the oxides (e.g., $MoO_3$, $WO_3$, $Re_2O_7$) as well as other materials such as acids, carbonates, sulfates, halides, oxyhalides, hydroxyhalides, hydroxides, sulfides, etc., of the metal. The cation forming the counter ion to the anion in the metal promoter compound is most suitably ammonium, although alkali metal or alkaline earth metal cations may also be utilized.

The support is optionally impregnated with one or more metal promoter compounds. This may be done at the same time that the other components of the catalyst are added or before and/or later. In one advantageous and convenient embodiment of the invention, the optional metal promoter compound(s), potassium salt and silver are incorporated into the catalyst simultaneously.

While not critical, it has generally been found that the minimum amount of metal promoter present in or deposited on the support or catalyst needed to measurably improve catalyst performance is approximately 0.1 weight percent metal (measured as the element irrespective of the form in which the promoter is present) based on the total weight of the supported silver catalyst where the metal is selected from the group consisting of W, Mo, Re and combinations thereof. Generally speaking, the maximum amount of metal promoter will be 10 weight percent. Operation within the range of 0.2 to 2.5 weight of metal promoter is particularly advantageous.

The degree of benefit obtained within the above-defined limits will vary depending upon particular properties and characteristics, such as, for example, reaction conditions, catalyst preparative techniques, surface area and pore structure and surface chemical properties of the support utilized, silver content of the catalyst, and potassium content of the catalyst.

The presence of the indicated and claimed amounts of optional metal promoters in this specification and claims does not preclude the use of other activators, promoters, enhancers, stabilizers, improvers, and the like.

The metal promoter compounds optionally used in the preparation of the instant catalysts are preferably compounds that can be solubilized in an appropriate solvent. Preferably, the solvent is a water-containing solvent. More preferably the solvent is the same solvent used to deposit the silver compound and potassium salt.

It is essential that the supported silver catalyst prepared as previously described herein be pretreated by exposure to a gaseous stream comprised of both one or more $C_1$–$C_{10}$ organic chlorides and molecular oxygen at a temperature of at least 150° C. (preferably, at least 200° C., most preferably, at least 220° C.) but no greater than 350° C. (preferably, no greater than 300° C., most preferably, no greater than 280° C.). The pretreatment step of the method claimed herein may conveniently be performed in the same apparatus or reactor in which the epoxidation step is carried out, for example, as part of the start-up of a propylene oxide plant or, if so desired, in a different vessel of suitable configuration. It will generally be advantageous to deploy the untreated catalyst in the form of a fixed bed and to pass the gaseous stream containing the organic chloride through the fixed catalyst bed in a substantially continuous manner. Gas hourly space velocities of from about 100 to 10,000 $hr^{-1}$ are typically preferred. Such contacting is continued for a time sufficient to permit the catalyst to accumulate the desired amount of chloride. While the exact mechanism of chloride incorporation is not known, it appears as though the organic chloride is somehow converted into a relatively non-volatile, water-insoluble form, perhaps by transfer of the chloride from the organic chloride to inorganic components of the catalyst such as the metallic silver. It is believed that at least some of the chloride is incorporated in the form of silver (I) chloride (AgCl).

Generally speaking, it will be desirable to adjust the parameters of the conditioning step such that at least 0.1 weight % Cl, more preferably at least about 0.5 weight % Cl, is incorporated in the chloride-containing catalyst. Typically, little additional benefit is realized by increasing the Cl content beyond 2 weight percent based on the total weight of the catalyst. The concentration of organic chloride in the treatment stream, while not critical, is suitably in the range of from 25 to 2000 ppm, although lower or higher concentrations could also be used. The treatment time generally will range from about 1 to 24 hours, depending upon, among other factors, temperature, organic chloride concentration, and the reactivity of the organic chloride employed.

The organic chloride is selected from those organic compounds containing from 1 to 10 carbon atoms and at least one chlorine atom. Other elements such as hydrogen, oxygen, nitrogen, sulfur, and halogens other than chlorine may also be present, but preferably the organic chloride consists only of hydrogen, carbon and chlorine atoms or only of carbon and chlorine atoms. Saturated organic chlorides are generally preferred for use. Illustrative organic chlorides include, but are not limited to, methyl chloride, ethyl chloride (an especially preferred organic chloride), propyl chloride, butyl chloride, methylene chloride, chloroform, carbon tetrachloride, ethylene dichloride, vinyl chloride, chloro cyclohexane, chlorobenzene, and the like.

It has surprisingly been discovered that the presence of molecular oxygen in the treatment stream is essential for purposes of improving the performance of the catalyst. Pretreatment with organic chloride alone has little or no beneficial effect. The treatment stream thus is suitably comprised of at least 1 volume % $O_2$ Exceptionally high levels of molecular oxygen in the treatment stream will generally be undesirable for safety or economic reasons. Typically, no more than about 10 vol. % $O_2$ is utilized. The balance of the treatment stream may be an inert gas such as nitrogen or the like, although non-chlorinated hydrocarbons such as propylene, methane, and the like could also be present. Generally, however, pretreatment is most rapidly and effectively achieved using a treatment stream which is essentially free of propylene or other reactive olefins. Thus, in one desirable embodiment, the treatment stream consists essentially of organic chloride, molecular oxygen, and an inert ballast gas.

The supported silver catalyst may additionally be treated with other substances in addition to the organic chloride, either prior to, during, or subsequent to the organic chloride pretreatment step in order to further improve or optimize its catalytic properties. For example, the catalyst may be contacted with carbon dioxide and/or a nitrogen oxide species. Suitable carbon dioxide treatment conditions include contacting the catalyst with a gaseous stream containing 5 to 60 vol. percent $CO_2$ at a temperature of from 150° C. to 350° C. It will generally be beneficial to also have molecular oxygen present together with the carbon dioxide. Catalysts treated with a stream containing both $CO_2$ and $O_2$ tend to maintain high selectivity, activity, and productivity over a longer period of time than catalysts treated with $CO_2$ alone. Oxygen concentrations of from 1 to 10 volume percent are typically suitable for such purposes. In a preferred embodiment, no propylene is present in the carbon dioxide treatment stream. Examples of nitrogen oxide species suitable for use include NO, $NO_2$, $N_2O_4$, $N_2O_3$ or mixtures thereof, with NO being the most preferred nitrogen oxide species. Typically, the concentration of the nitrogen oxide species in the gaseous stream used to treat the supported silver catalyst will be in the range of about 10 to 2000 ppm. Temperatures of from 150° C. to 350° C. are usually sufficient for this purpose.

In the epoxidation step of this invention, a feedstream comprising propylene and molecular oxygen is contacted with the previously described organic chloride-treated catalyst in a reactor under conditions effective to accomplish at least partial oxidation of the propylene to the corresponding epoxide. Typical epoxidation conditions include temperatures within the reaction zone of the reactor on the order of about 180° to 350° C. (more preferably, 200° to 300° C.) and pressures from about 1 to about 60 atmospheres. An important advantage of the present process is that the feedstream need not contain any organic chloride or other chloride- or halogen-containing substance in order to attain high efficiency. That is, high selectivity to propylene oxide is observed even when the feedstream is essentially free of any gaseous chloride species. In a particularly preferred embodiment of the invention, the feedstream contains less than 1 ppm organic chloride, with 0 ppm organic chloride also being operable. It may, however, be desirable to periodically reactivate or regenerate the catalyst following an extended period of epoxidation by co-feeding organic chloride (preferably 1 to 2000 ppm) with the feedstream. For example, once the chloride content of the catalyst being used drops below a level sufficient to provide the desired level of catalyst performance, the organic chloride treatment step may be repeated with the used catalyst. The feedstream may also contain carbon dioxide, which generally helps increase epoxide selectivity. A gaseous nitrogen oxide species may also be supplied to the reaction zone within the reactor by introducing said species to the feedstream containing propylene (fresh and/or recycled) and molecular oxygen.

The introduction of gaseous nitrogen oxide species, while not mandatory, is extremely beneficial to epoxidation performance as it helps to promote a relatively high level of catalytic activity without sacrificing propylene oxide selectivity. The optimum amount is determined, in part, by the particular potassium salt and metal promoter compound (if any) used and the concentrations thereof, and by other factors noted above which influence the optimum amount of potassium salt and metal promoter. Typically, a suitable concentration of the nitrogen oxide species for epoxidation of propylene is about 0.1 to about 2,000 ppm by volume.

The "oxygen" employed in the reaction may be defined as including pure molecular oxygen, atomic oxygen, any transient radical species derived from atomic or molecular oxygen capable of existence under epoxidation conditions, mixtures of another gaseous substance with at least one of the foregoing, and substances capable of forming one of the foregoing under epoxidation conditions. The oxygen is typically introduced to the reactor either as air, commercially pure oxygen or other substance which under epoxidation conditions both exists in a gaseous state and forms molecular oxygen.

The gaseous components which are supplied to the reaction zone, or that region of the reactor where reactants and catalyst are brought together under epoxidation conditions, are generally combined before being introduced to the reactor. If desired, however, such components may alternatively be introduced separately or in various combinations. The feedstream having the particular composition previously described thus may be formed prior to or at the time the individual components thereof enter the reaction zone. The feedstream may utilize or incorporate a recycle stream from the reactor. The use of the term "feedstream" herein thus is not meant to limit the present process to the embodiment where all of the gaseous components are combined prior to introduction of said components into the reaction zone. The reactors in which the process and catalyst of the present invention are employed may be of any type known to the art.

The feedstream may also contain a ballast or diluent, such as nitrogen or other inert gas, particularly when air is used as the source of oxygen. Varying amounts of water vapor may also be present.

The components of the feedstream are most suitably present in the amounts shown in the following table:

| Component | Volume in % (or ppm) for Propylene Oxidation |
| --- | --- |
| propylene | about 2 to about 50% |
| oxygen | about 2 to about 10% |
| organic chloride | <1 ppm, more preferably, 0 |
| nitrogen oxide species | 0 to about 2,000 ppm |
| carbon dioxide | 0 to 60%, more preferably 5 to 50% |
| nitrogen or other ballast gas | remainder. |

Although the present invention can be used with any size and type of vapor phase epoxidation reactor, including both fixed bed and fluidized bed reactors known to the art, it is contemplated that the present invention will find most widespread application in standard fixed bed, multi-tubular reactors such as those now in use as ethylene oxide reactors. These generally include wall-cooled as well as adiabatic or non-wall-cooled reactors. The conditioning and epoxidation steps may be conveniently carried out in the same reactor, as there will generally be no need to use different equipment for each step. This will minimize the amount of time required to start up and operate (including periodic reactivation of the catalyst with organic chloride) an epoxidation unit. Tube lengths may typically range from about 5 to about 60 feet but will frequently be in the range of from about 15 to about 45 feet. The tubes may have internal diameters from about 0.5 to about 2.5 inches and are expected to be typically from about 0.8 to about 1.5 inches. A plurality of tubes packed with catalyst arranged in parallel within a suitable shell may be employed. GHSV generally ranges from about 500 to about 10,000 $hr^{-1}$. Typically GHSV values range from about 800 to about 3,000 $hour^{-1}$ at pressures from about 1 to about 60 atmospheres, commonly about 1.1 to about 30 atmospheres. Contact times should be sufficient to convert 0.5 to 70%, preferably 5 to 30%, of the propylene.

EXAMPLES

Example 1 (Comparative)

This example demonstrates that the use of a treatment stream containing ethyl chloride but no molecular oxygen fails to yield a supported silver catalyst capable of converting propylene to propylene oxide in the absence of nitrogen oxide species and organic chloride in the propylene feedstream.

A catalyst supported on calcium carbonate containing 51 weight % Ag, 17 weight % Ca, 0.53 weight % Mo (from $(NH_4)_2Mo_2O_7$), 1.7 weight % K (from $KNO_3$, added sequentially after impregnation of the support with silver compound and calcination), 0.68 weight % N, and less than 0.05 weight % Cl was prepared in accordance with the procedure described in U.S. Pat. No. 5,625,084. Approximately 5 cc of the catalyst was loaded into a 0.5 inch outside diameter 316 stainless steel tubular reactor and then pretreated as follows for 20 hours: 250° C., 30 psig, 500 ppm ethyl chloride in treatment stream (balance $N_2$), 1200$hr_{-1}$ GHSV. A feedstream containing 4.0 vol % propylene, 8.0 vol % $O_2$ and 14.9 vol % $CO_2$ was then passed over the catalyst at 232° C. and 100 psig at a GHSV of 1200 $hr^{-1}$. After 19.5 hours under such conditions, the propylene conversion was 5.0% while the selectivity to propylene oxide was 0%. The used catalyst was found to contain <0.05 weight % Cl.

Example 2

This example demonstrates the beneficial effect of pretreating a supported silver catalyst with a mixture of ethyl chloride and molecular oxygen.

In accordance with the procedures described in U.S. Pat. No. 5,625,084, a supported silver catalyst was prepared having the following elemental composition: 48 weight % Ag, 15 weight % Ca (from calcium carbonate support), 0.59 weight % Mo (from $(NH_4)_2Mo_2O_7$), 1.8 weight % K (from $KNO_3$, added after calcination as in Example 1), 0.67 weight % N, 5.5 weight % C. (from calcium carbonate support), and <0.05 weight % Cl. Approximately 10 cc of the catalyst was loaded into a 0.75 inch outside diameter 316 stainless steel tubular reactor and exposed for 20 hours at 250° C. and 30 psig to a treatment stream containing 5.21 vol % $O_2$ and 500 ppm (vol.) ethyl chloride (balance $N_2$) (GHSV =1200 $hr^{-1}$). Ethyl chloride treatment was then discontinued and a feedstream containing 4.6 vol % propylene and 7.6 vol % $O_2$ passed over the catalyst bed at 216° C., 300 psig, and 4800 $hr^-$GHSV. After 16 hours under such conditions the pretreated catalyst exhibited propylene conversion of 3.8% and a selectivity to propylene oxide of 59%. The catalyst was analyzed after 123.5 hours under a variety of operating conditions (all 0 ppm ethyl chloride, 0–10 ppm NO) and found to still contain 0.5 weight % Cl.

Example 3

This example demonstrates the effect of adding carbon dioxide to the feedstream of an epoxidation process utilizing a supported catalyst which has been treated with an organic chloride in accordance with the present invention.

A silver catalyst supported on calcium carbonate was prepared following the procedures described in U.S. Pat. No. 5,625,084. The elemental composition of the catalyst was as follows: 44 weight % Ag, 18 weight % Ca, 0.44 weight %

Mo (from $(NH_4)_2Mo_2O_7$), 1.7 weight % K (from $KNO_3$, added after calcination), 1.28 weight % N, and <0.05 weight % Cl. Pretreatment with ethyl chloride was performed for 21 hours at 250° C. and 30 psig using a treatment stream containing 5.1 vol % $O_2$ and 500 ppm ethyl chloride (1200 $hr^{-1}$ GHSV, balance $N_2$). Propylene epoxidation was then performed at 232° C. and 100 psig using ca. 5cc of catalyst in a 0.5 in. outside diameter 316 stainless steel tubular reactor; the feedstream contained varying amounts of carbon dioxide, propylene and oxygen, but no NO or ethyl chloride. The GHSV was 2400 $hr^{-1}$. The results observed are summarized in the following table.

| Epoxidation Condition | Time at Condition, hr | Propylene, vol % | $O_2$ vol % | $CO_2$ vol % | PO Selectivity % | Propylene Conv., % | PO Productivity lb/hr·ft³ |
|---|---|---|---|---|---|---|---|
| A | 102.2 | 4.10 | 8.12 | 14.43 | 60 | 3.2 | 0.36 |
| B | 37.5 | 4.15 | 8.15 | 0 | 51 | 9.1 | 0.70 |
| C | 42.0 | 4.09 | 7.97 | 14.48 | 64 | 3.9 | 0.36 |

Example 4

Example 3 was repeated, except that the freshly prepared supported silver catalyst was pretreated with ethyl chloride for 18 hours and the treatment stream contained 5.2 vol % $O_2$. The pretreated catalyst was evaluated using a feedstream comprised of 8.15 vol % propylene, 6.35 vol % $O_2$ and 14.8 vol % $CO_2$ (GHSV =1200 $hr^1$, balance $N_2$) at 250° C. and 100 psig.

After 45 hours of operation under these epoxidation conditions, propylene conversion of 6.5% and propylene oxide selectivity of 52% (0.5 lb PO/hr·ft³) were obtained. The used catalyst contained 1.0 weight % Cl (<150 ppm water-soluble chloride).

Example 5

This example shows that other gases besides oxygen, organic chloride, and nitrogen may be present during the organic chloride-treatment step. The freshly prepared catalyst of Example 3 was pretreated with ethyl chloride for 30 hours at 250° C. and 30 psig using a treatment stream containing 10.7 vol % propylene, 5.2 vol % $O_2$, 200 ppm NO and 500 ppm ethyl chloride (GHSV =1200 $hr^{-1}$, balance $N_2$). Propylene oxide selectivity of 42.6% and propylene conversion of 10.6% (0.66 lb PO/hr·ft³) were obtained. After pretreatment in this manner, the catalyst was then evaluated as an epoxidation catalyst at 232° C. and 100 psig using a feedstream containing no ethyl chloride. The feedstream had the following composition: 9.3 vol % propylene, 6.4 vol % $O_2$, 380 ppm NO and 13.8 vol % $CO_2$ (GHSV =2840 $hr^{-1}$). After 13.5 hours of operation under such conditions, the propylene oxide selectivity was 53.2%, the propylene conversion was 2.8%, and the propylene oxide productivity was 0.58 lb PO/hr·ft³. After operating for a total of 170 hours under different conditions with 0–10 ppm ethyl chloride and 50–731 ppm NO in the feedstream, the catalyst contained 0.2 weight % Cl by elemental analysis. Example 6

This example demonstrates the practice of successively treating a supported silver catalyst with ethyl chloride and then carbon dioxide prior to using the catalyst for epoxidation purposes.

A catalyst was prepared in accordance with U.S. Pat. No. 5,625,084 having an elemental composition of 51 weight % Ag, 17 weight % Ca (from calcium carbonate), 0.51 weight % Mo (from $(NH_4)_2Mo_2O_7$), 2.1 weight % K (from potassium nitrate, added sequentially after calcination), and 0.94 weight % N. The catalyst was first treated for 20 hours at 250° C. and 30 psig using a treatment stream containing 5.0 mol % $O_2$ and 500 ppm ethyl chloride (GHSV=1200 $hr^{-1}$) in a back-mixed reactor. The catalyst was thereafter treated for an additional 4.2 hours at 250° C. and 30 psig with a treatment stream containing 5.0 vol % $O_2$ and 50.0 vol % $CO_2$ (GHSV=1200 $hr^{-1}$). A feedstream containing 4.0 vol % propylene and 8.0 vol % $O_2$ (no NO or ethyl chloride) was then passed over the pretreated catalyst at the same temperature, pressure and GHSV. After 20.8 hours, the propylene oxide selectivity was 54%, the propylene conversion was 10%, and the propylene oxide productivity was 0.45 lb PO/hr·ft³. The used catalyst contained 0.85 weight % Cl by elemental analysis.

By way of comparison, a catalyst of similar composition was pretreated with ethyl chloride as described above but was not subjected to carbon dioxide pretreatment. The catalyst thus obtained exhibited a maximum propylene conversion of 3.5% and a maximum propylene oxide selectivity of 50%, but lost essentially all its activity within a several day period. Example 7

The procedure of Example 6 was repeated, except that in the carbon dioxide pretreatment step, the treatment stream contained 10.0 vol % $CO_2$ and no oxygen and pretreatment was carried out for 3.0 hours instead of 4.2 hours. Propylene epoxidation was performed at 232° C. and 30 psig using a feedstream containing 4 vol % propylene, and 8 vol % $O_2$ (balance $N_2$, GHSV=1200$hr^{-1}$). After 70.0 hours, propylene oxide selectivity was 48%, propylene conversion was 7.5%, and PO productivity was 0.24 lb PO/hr·ft³. The used catalyst contained 0.8 weight % Cl by elemental analysis.

Example 8

The use of a tungsten-promoted supported silver catalyst pretreated with ethyl chloride and oxygen in accordance with the present invention is illustrated by this example.

The catalyst was prepared by impregnation of calcium carbonate with solutions of silver (I) oxide and $(NH_4)_{10}W_{12}O_{41}$, calcination, and then impregnation with potassium nitrate. By elemental analysis, the catalyst had the following composition: 39 weight % Ag, 0.6 weight % W and 2.3 weight % K. Approximately 5 cc of the catalyst was loaded into a 0.5 inch outside diameter 316 stainless steel tubular reactor and treated for 20 hours at 250° C. and 30 psig using a treatment stream containing 5.0 vol % $O_2$ and 500 ppm ethyl chloride (GHSV =1200 $hr^{-1}$). A feedstream containing 4.0 vol % propylene, 8.0 vol % $O_2$ and 15.0 vol % $CO_2$ was passed over the pretreated catalyst at 232° C. and 100 psig (GHSV =2400$hr^{-1}$). After 93.3 hours of operation under such conditions, the propylene oxide selectivity was 55%, the propylene conversion was 8%, and the PO productivity was 0.26 lb PO/hr·ft³. The used catalyst contained 0.9 weight % Cl.

Example 9

This example demonstrates an embodiment of the invention wherein a supported silver catalyst is first treated with NO and $O_2$ and then with ethyl chloride and $O_2$. The catalyst was prepared in accordance with the procedures described in U.S. Pat. No. 5,625,084 and had an initial elemental composition of 52 weight % Ag, 20 weight % Ca (from the calcium carbonate support), 0.55 weight % Mo (from $(NH_4)_2Mo_2O_7$), 1.8 weight % K (from $KNO_3$, applied after calcination), 1.04 weight % N, and <0.05 weight % Cl. Using a 0.5 inch outside diameter 316 stainless steel tubular reactor, approximately 5 cc of catalyst was exposed at 250° C. and 30 psig to a treatment stream containing 5.0 vol % $O_2$ and 200 ppm NO (GHSV =1200hr$^{-1}$). After 20 hours, the treatment stream composition was changed to 5.0 vol % $O_2$ and 500 ppm ethyl chloride (all other conditions remained the same). After another 23.3 hours, propylene epoxidation was commenced. Different epoxidation conditions (30 psig, 4.0 vol % propylene, 8.0 vol % $O_2$, 1200 hr$^{-1}$ GHSV, no NO or ethyl chloride) were evaluated as summarized in the following table:

| Epoxidation Condition | Time at Condition, hr | T. °C. | $CO_2$, vol % | PO Selectivity % | Propylene Conv., % | PO Productivity lb/hr.ft$^3$ |
|---|---|---|---|---|---|---|
| A | 18.3 | 250 | 15.0 | 70→62 | 2.0 | 0.20 |
| B | 18.3 | 250 | 0 | 50 | 2→9 | 0.2→0.7 |
| C | 5.0 | 240 | 0 | 50 | 8 | 0.6 |

Example 10

This example demonstrates the use of a supported silver catalyst containing rhenium and molybdenum promoters in the process of this invention. The catalyst was prepared by impregnating calcium carbonate support with solutions of $(NH_4)_2ReO_4$, $(NH_4)_2MoO_4$, a silver compound, and potassium nitrate and calcining, following the procedures described in U.S. Pat. No. 5,625,084. The catalyst thus obtained had an elemental composition of 0.5 weight % Re, 50 weight % Ag, 0.5 weight % Mo, 2 weight % K, and 0.69 weight % N. Ethyl chloride pretreatment was performed on a 5 cc sample of catalyst in a 0.5 in. outside diameter 316 SS reactor tube for 22 hours at 250° C. and 30 psig using a treatment stream containing 5.0 vol % $O_2$ and 500 ppm ethyl chloride (GHSV=1200 hr$^{-1}$). Thereafter, propylene epoxidation was practiced under the following conditions: 250° C., 30 psig, 10.0 vol % propylene, 5.0 vol % $O_2$, 200 ppm NO, 1200 hr$^{-1}$ GHSV. The ethyl chloride and carbon dioxide levels in the feedstream were varied as indicated in the following table.

| Epoxidation Condition | Time at Condition, hr | EtCl, ppm | $CO_2$, vol % | PO Selectivity % | Propylene Conv., % | PO Productivity lb/hr.ft$^3$ |
|---|---|---|---|---|---|---|
| A | 92 | 0 | 0 | 41.8 | 5.0 | 0.4 |
| B | 18 | 0 | 9.6 | 63.2 | 1.6 | 0.2 |
| C | 49 | 50 | 9.6 | 63.8 | 2.2 | 0.3 |
| D | 15 | 0 | 0 | 44.3 | 5.4 | 0.5 |

We claim:

1. A propylene epoxidation process comprising:
   (a) contacting a supported silver catalyst with a treatment stream comprised of a $C_1$–$C_{10}$ organic chloride and molecular oxygen in the vapor phase at a temperature of from 150° C. to 350° C. for a time effective to incorporate chloride into the supported silver catalyst to form a chloride-containing catalyst, wherein the supported silver catalyst is comprised of (i) an inert refractory solid support, (ii) a catalytically effective amount of silver, and (iii) a promoting amount of a potassium promoter derived from a potassium salt comprising potassium cation and a nitrogen oxyanion or precursor thereof; and
   (b) contacting the chloride-containing catalyst with a feedstream comprised of propylene and molecular oxygen, but essentially free of $C_1$–$C_{10}$ organic chloride, for a time and at a temperature effective to form propylene oxide.

2. The process of claim 1 wherein the inert refractory solid support is comprised of an alkaline earth metal carbonate.

3. The process of claim 1 wherein the treatment stream is comprised of from 25 to 2000 ppm of the $C_1$–$C_{10}$ organic chloride.

4. The process of claim 1 wherein the supported silver catalyst is additionally comprised of a promoting amount of a metal selected from the group consisting of molybdenum, rhenium, tungsten and mixtures thereof.

5. The process of claim 1 wherein the treatment stream is essentially free of propylene.

6. The process of claim 1 wherein the feedstream is additionally comprised of a nitrogen oxide species.

7. The process of claim 1 wherein after step (a) and before step (b) the chloride-containing catalyst is contacted with a carbon dioxide stream comprised of carbon dioxide at a temperature of from 150° C. to 350° C.

8. The process of claim 7 wherein the carbon dioxide stream is additionally comprised of molecular oxygen.

9. The process of claim 1 wherein the potassium salt is selected from the group consisting of potassium carbonate, potassium bicarbonate, potassium nitrate, potassium nitrite, and mixtures thereof.

10. The process of claim 1 comprising an additional step after step (b) of repeating step (a).

11. The process of claim 1 wherein the chloride-containing catalyst contains at least 0.5 weight % Cl.

12. The process of claim 1 wherein the $C_1$–$C_{10}$ organic chloride is ethyl chloride.

13. A propylene epoxidation process comprising:
   (a) contacting a supported silver catalyst with a treatment stream comprised of 25 to 2000 ppm of a $C_1$–$C_4$ organic chloride and molecular oxygen in the vapor phase at a temperature of from 220° C. to 280° C. for a time effective to incorporate chloride into the supported silver catalyst to form a chloride-containing catalyst containing at least 0.1 weight percent Cl, wherein the supported silver catalyst is comprised of (i) an inert refractory support comprised of an alkaline earth metal carbonate, (ii) from 10 to 60 weight percent silver, and (iii) a promoting amount of a potassium promoter derived from a potassium salt selected from the group consisting of potassium nitrate, potassium nitrite, potassium carbonate, potassium bicarbonate and mixtures thereof; and (b) contacting the chloride-containing catalyst with a feedstream comprised of propylene and molecular oxygen, but essentially free of $C_1$–$C_4$ organic chloride, at a temperature of from 220° C. to 280° C. for a time effective to form propylene oxide.

14. The process of claim 13 wherein the treatment stream is essentially free of propylene.

15. The process of claim 13 wherein the supported silver catalyst is additionally comprised of from 0.2 to 2.5 weight percent of a metal promoter selected from the group consisting of molybdenum, rhenium, tungsten and mixtures thereof.

16. The process of claim 13 wherein after step (a) and before step (b) the chloride-containing catalyst is contacted with a gaseous stream comprised of 5 to 60 volume percent carbon dioxide at a temperature of from 220° C. to 280° C.

17. The process of claim 16 wherein said gaseous stream is additionally comprised of from 1 to 10 volume percent molecular oxygen.

18. The process of claim 13 comprising an additional step after step (b) of repeating step (a).

19. The process of claim 13 wherein the alkaline earth metal carbonate is calcium carbonate.

20. The process of claim 13 wherein the $C_1$–$C_4$ organic chloride is ethyl chloride.

* * * * *